United States Patent
Matsuura

(10) Patent No.: US 10,064,989 B2
(45) Date of Patent: Sep. 4, 2018

(54) BLOOD PROCESSING FILTER AND BLOOD PROCESSING FILTER MANUFACTURING METHOD

(71) Applicant: ASAHI KASEI MEDICAL CO., LTD., Tokyo (JP)

(72) Inventor: Yoshimasa Matsuura, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 210 days.

(21) Appl. No.: 15/026,467

(22) PCT Filed: Oct. 2, 2014

(86) PCT No.: PCT/JP2014/076425
§ 371 (c)(1),
(2) Date: Mar. 31, 2016

(87) PCT Pub. No.: WO2015/050213
PCT Pub. Date: Apr. 9, 2015

(65) Prior Publication Data
US 2016/0235905 A1    Aug. 18, 2016

(30) Foreign Application Priority Data
Oct. 3, 2013 (JP) ................. 2013-208403

(51) Int. Cl.
*A61M 1/36* (2006.01)
*A61M 1/02* (2006.01)

(52) U.S. Cl.
CPC ........ *A61M 1/3636* (2014.02); *A61M 1/0281* (2013.01); *A61M 1/3635* (2014.02);
(Continued)

(58) Field of Classification Search
CPC . A61M 1/3636; A61M 1/3635; A61M 1/0281
See application file for complete search history.

(56) References Cited

U.S. PATENT DOCUMENTS 4,157,967 A    6/1979   Meyst et al.
4,170,056 A *  10/1979  Meyst ............... A61M 5/165
                                              210/446
(Continued)

FOREIGN PATENT DOCUMENTS

AU    5572080      6/1980
AU    526468       1/1983
(Continued)

OTHER PUBLICATIONS

Search Report issued in PCT/JP2014/076425, dated Nov. 11, 2014.
(Continued)

*Primary Examiner* — Chester T Barry
(74) *Attorney, Agent, or Firm* — Greenblum & Bernstein, P.L.C.

(57) ABSTRACT

A blood processing filter for removing undesirable components from liquid containing a blood component or blood, comprises: a sheet-shaped filter element; and a hard container that includes an inlet-side container element and an outlet-side container element that are disposed to clamp the filter element, and has an internal space separated by the filter element into an inlet space and an outlet space, wherein the filter element includes a filtering surface on a side of the inlet space, a filtering surface on a side of the outlet space, and an end surface along peripheries of the pair of filtering surfaces, the inlet-side container element and the outlet-side container element are provided with a gripper that clamps and compresses an outer edge portion of the pair of filtering surfaces, and a thickness of the filter element is compressed at the gripper to be 0.05 to 0.5 times the thickness.

11 Claims, 8 Drawing Sheets

(52) U.S. Cl.
CPC ............... *A61M 2202/0439* (2013.01); *A61M 2205/7545* (2013.01); *A61M 2207/00* (2013.01)

(56) References Cited

U.S. PATENT DOCUMENTS

| | | |
|---|---|---|
| 5,688,460 A | 11/1997 | Ruschke |
| 5,723,047 A | 3/1998 | Turnbull |
| 5,772,831 A | 6/1998 | Moro et al. |
| 6,032,807 A | 3/2000 | Sternberg et al. |
| 6,143,174 A | 11/2000 | Graus |
| 7,534,348 B2 | 5/2009 | Reitz et al. |
| 2004/0226886 A1 | 11/2004 | Hester et al. |
| 2005/0056580 A1 | 3/2005 | Reitz et al. |
| 2006/0049097 A1 | 3/2006 | Cavallini et al. |
| 2006/0108272 A1 | 5/2006 | Ariagno et al. |
| 2009/0221781 A1* | 9/2009 | Ashby ............... A61L 27/18 526/318.2 |
| 2012/0067811 A1 | 3/2012 | Yokomizo et al. |

FOREIGN PATENT DOCUMENTS

| | | |
|---|---|---|
| EP | 0526678 | 2/1993 |
| GB | 2266477 | 11/1993 |
| JP | 52-116969 | 9/1977 |
| JP | 6-79110 | 3/1994 |
| JP | 7-267871 | 10/1995 |
| JP | 9-168703 | 6/1997 |
| JP | 11-216179 | 8/1999 |
| JP | 2000-517240 | 12/2000 |
| JP | 4891080 | 3/2012 |
| WO | 95/17236 | 6/1995 |
| WO | 2004/050147 | 6/2004 |
| WO | 2012/039402 | 3/2012 |

OTHER PUBLICATIONS

International Preliminary Report on Patentability issued in PCT/JP2014/076425, dated Apr. 14, 2016.

Search Report issued in European Patent Office (EPO) Patent Application No. 14850445.9, dated Sep. 9, 2016.

\* cited by examiner

BLOOD PROCESSING FILTER AND BLOOD PROCESSING FILTER MANUFACTURING METHOD

TECHNICAL FIELD

The present invention relates to a blood processing filter for removing undesirable components, such as aggregates and leukocytes, from liquid containing blood components or blood, and to a blood processing filter manufacturing method. In particular, the present invention relates to a disposable blood processing filter for removing microaggregates and leukocytes which may cause side effects, from whole blood preparations, erythrocyte preparations, thrombocyte preparations, blood plasma preparations and the like for blood transfusion, as well as a method for manufacturing the blood processing filter.

BACKGROUND ART

It is becoming common for whole blood collected from a donor to be separated into blood component preparations, such as an erythrocyte preparation, a thrombocyte preparation, and a blood plasma preparation, stored and then provided for transfusion. Since microaggregates and leukocytes included in these blood preparations cause various side effects of blood transfusion, many methods of removing these undesirable components before blood transfusion and then performing transfusion, or performing transfusion with preparations with undesirable components having been removed after blood collection and then temporarily been stored, have been widely used.

Among methods of removing these undesirable components from blood preparations, treatment of blood preparations through a blood processing filter is most typical. Two types of blood processing filters are used; one is what includes a filter element made of nonwoven fabric or a porous body equipped in, for example, a flexible container as described in Patent Literatures 1 to 5, and the other is what includes the filter element equipped in a hard container made of polycarbonate or the like.

Typically, for treatment of a blood preparation through a blood processing filter, a blood preparation bag containing the blood preparation to be processed is connected to an inlet of the blood processing filter, the blood preparation bag is placed at a position higher than the blood processing filter by approximately 20 to 100 cm, thereby introducing the blood preparation from the blood preparation bag into the blood processing filter due to the action of gravity. On the other hand, a recovery bag for storing a filtered blood preparation is connected to an outlet of the blood processing filter, and the recovery bag is placed at a position lower than the blood processing filter by approximately 50 to 100 cm, thereby storing the filtered blood preparation into the recovery bag due to the action of gravity. At this time, a pressure loss occurs due to the resistance of the filter element, in a space in the blood processing filter container on the inlet side of the filter element, thereby causing a positive pressure. On the contrary, in a space on the outlet side of the filter element, the blood preparation flows from the outlet, thereby causing a negative pressure.

Since a blood processing filter with a flexible container as shown in Patent Literatures 1 to 5 has a container that is flexible, the space on the inlet side swells like a balloon owing to a positive pressure, and the filter element is pressed against the outlet side of the container. On the other hand, in the space on the outlet side, the container is in close contact with the filter element owing to the negative pressure, and the state is brought into that where the opening of the outlet is blocked. That is, since blood tends to flow from the inside of the filter but the opening is blocked, it is difficult for the blood to flow out.

On the contrary, a blood processing filter through use of a hard container does not largely deform even during filtering, and the state is not brought into that where the filter element is pressed against the outlet side to block the opening of the outlet. Such a hard container includes an inlet-side container element and an outlet-side container element which are fitted with each other, and rib-shaped convexes provided for the inlet-side container element and the outlet-side container element are pressed against each other, thereby clamping the outer edge portion of the filter element.

CITATION LIST

Patent Literature

[Patent Literature 1] Japanese Unexamined Patent Publication No. H11-216179
[Patent Literature 2] Japanese Unexamined Patent Publication No. H7-267871
[Patent Literature 3] International Publication No. 2004/050147
[Patent Literature 4] International Publication No. 95/17236
[Patent Literature 5] European Unexamined Patent Publication No. 0526678.

SUMMARY OF INVENTION

Technical Problem

However, in the case of the blood processing filter including such a hard container, the relationship between the degree of compression of the outer edge portion of the filter element and the removal efficiency of undesirable components is not considered. Consequently, in order to securely remove undesirable components, for example, a scheme for increasing the compression region at penalty in effective filtering area and the like is required, and it is difficult to facilitate improvement in blood treatment efficiency.

Thus, a first aspect of the present invention has an object to provide a blood processing filter that can easily avoid the risk of incomplete removal of undesirable components without reducing the blood treatment efficiency, and to provide a blood processing filter manufacturing method.

In the above background art, an ultrasonic bonding method is mainly used for adhesion of the hard container. However, in view of energy transmission efficiency, only the peripheral portion is pressed and bonded. Consequently, deformation of the container easily occurs. There is a tendency where, in both the filter and the filter element after molding, the central portion is thick and the peripheral side is thin, and the blood flow during blood treatment becomes uneven.

Thus, a second aspect of the present invention has an object to provide a blood processing filter that can uniformly use the entire filter element, and a blood processing filter manufacturing method.

Solution to Problem

The present inventors have diligently researched to solve the above problems, and, as a result, have found that undesirable components can be positively removed within a desired range by not only clamping and simply compressing the outer edge portion of the filtering surfaces on the front and back of the filter element with a gripper of a hard container but also compressing the filter element to be 0.05 to 0.5 times the thickness, and thus reached the first aspect of the present invention.

That is, the first aspect of the present invention is a blood processing filter for removing undesirable components from liquid containing a blood component or blood, the filter comprising: a sheet-shaped filter element; and a hard container that includes an inlet-side container element and an outlet-side container element that are disposed to clamp the filter element, and has an internal space separated by the filter element into an inlet space and an outlet space, wherein the filter element includes a filtering surface on a side of the inlet space, a filtering surface on a side of the outlet space, and an end surface along peripheries of the pair of filtering surfaces, the inlet-side container element and the outlet-side container element are provided with a gripper that clamps and compresses an outer edge portion of the pair of filtering surfaces, and a thickness of the filter element is compressed by the gripper to be 0.05 to 0.5 times the thickness.

The blood processing filter can prevent a side leakage (side flow) where undesirable components flow over the outer edge portion of the filter element without being filtered, by the gripper that compresses the filter element to have a thickness that is 0.05 to 0.5 times the thickness. As a result, the region of the outer edge portion compressed by the gripper can be facilitated to be reduced. Consequently, the risk of incomplete removal of undesirable components can be easily avoided without reducing the blood treatment efficiency.

Furthermore, in the blood processing filter according to the first aspect, it is preferred that the gripper compress the filter element at a range with a width of 1 to 5 mm from an outermost edge, as the outer edge portion. These can prevent the filter element from being apart from the gripper, and facilitate designing within an allowable range in view of blood treatment efficiency or economically.

Furthermore, in the blood processing filter according to the first aspect, it is preferred that at least one of the inlet-side container element and the outlet-side container element be provided with a rib on an inner surface, and a coefficient of variation value (CV value) of the thickness of the filter element be 6% or less. According to this blood processing filter, the entire filter element can be effectively utilized.

Furthermore, in the blood processing filter according to the first aspect, it is preferred that the coefficient of variation value (CV value) of a distance from the inlet-side container element to an inlet-side surface of the filter element in the inlet space be 10% or less. According to this blood processing filter, blood having entered from the inlet evenly spreads into the inlet space, and the filter element can be effectively used.

The second aspect of the present invention is a blood processing filter for removing undesirable components from liquid containing a blood component or blood, the filter comprising: a sheet-shaped filter element; and a hard container that includes an inlet-side container element and an outlet-side container element that are disposed to clamp the filter element, and has an internal space separated by the filter element into an inlet space and an outlet space, wherein the filter element includes a filtering surface on a side of the inlet space, a filtering surface on a side of the outlet space, and an end surface along peripheries of the pair of filtering surfaces, the inlet-side container element and the outlet-side container element are provided with a gripper that clamps and compresses an outer edge portion of the pair of filtering surfaces, at least one of the inlet-side container element and the outlet-side container element is provided with a rib on an inner surface, and a coefficient of variation value (CV value) of a thickness of the filter element is 6% or less.

In the case where the difference in thickness among positions of the filter element is large during filtering blood and the like, the resistance of a thick portion that is a portion with a low bulk density is low, and the blood and the like pass only through thick portions of the filter element. Consequently, a lopsided flow easily occurs, which causes a risk that not the entire filter can be used. Unlike this, since the blood processing filter according to the second aspect sets the coefficient of variation value of the thickness of the filter element to 6% or less, the lopsided flow of blood and the like can be prevented, and the entire filter element can be utilized.

Furthermore, in the blood processing filter according to the second aspect, it is preferred that the coefficient of variation value of a distance from the inlet-side container element to an inlet-side surface of the filter element in the inlet space be 10% or less. According to this blood processing filter, blood having entered from the inlet evenly spreads into the inlet space, and the filter element can be effectively used.

Furthermore, it is preferred that the thickness of the filter element according to the second aspect be compressed by the gripper to be 0.05 to 0.5 times the thickness. This blood processing filter can easily avoid the risk of incomplete removal of undesirable components without reducing the blood treatment efficiency.

Furthermore, it is preferred that the gripper of the blood processing filter according to the second aspect compress the filter element at a range with a width of 1 to 5 mm from the outermost edge, as an outer edge portion. This blood processing filter can prevent the filter element from being apart from the gripper, and facilitate designing within an allowable range in view of blood treatment efficiency or economically.

Furthermore, it is preferred that each of the grippers of the blood processing filter according to the first aspect and the second aspect be in close contact with the end surface of the filter element. The gripper is positioned so as to be in close contact with the end surface. Consequently, the filter element is resistant to deviate, which is advantageous in high-density compression of the outer edge portion of the pair of filtering surfaces against each other.

Furthermore, in the blood processing filters according to the first aspect and the second aspect, it is preferred that the inlet-side container element and the outlet-side container element further include a fitting part from fitting portions surrounding the end surface of the filter element and fitted to one another. This facilitates positioning and joining of the inlet-side container element and the outlet-side container element.

Furthermore, in the blood processing filter, it is preferred that the fitting portion include an inlet-side fitting portion provided at the inlet-side container element, and an outlet-side fitting portion provided at the outlet-side container element, and at least a part of a sliding surface between the inlet-side fitting portion and the outlet-side fitting portion be bonded in a belt shaped manner along an entire periphery of the fitting portion with the melt resin. Thus, the airtightness and liquid-tightness are increased.

Furthermore, it is preferred that the sliding surface of the blood processing filter be provided with a resin flow path, the resin flow path be filled with the melt resin to bond the sliding surface. Thus, the melt resin is resistant to deviate from the sliding surface, and has no possibility of entering the inside of the hard container.

Furthermore, in the blood processing filters according to the first aspect and the second aspect, it is preferred that the hard container be made of resin with a Young's modulus of at least 1 GPa at room temperature. This can prevent deformation during filtering.

A method of manufacturing a blood processing filter according to the first aspect of the present invention is a method of manufacturing a blood processing filter for removing undesirable components from liquid containing a blood component or blood, the method comprising: an injection molding step of injection-molding an inlet-side container element using one mold, and an outlet-side container element using another mold; a inserting step of inserting a filter element into the inlet-side container element or the outlet-side container element; a fitting step of mold-fitting the molds, and fitting the inlet-side container element and the outlet-side container element to each other; and a bonding step of bonding the inlet-side container element and the outlet-side container element to each other with melt resin, wherein the filter element includes a pair of filtering surfaces, and an end surface along peripheries of the pair of the filtering surfaces, the inlet-side container element and the outlet-side container-element are provided with a gripper that clamps and compresses an outer edge portion of the pair of filtering surfaces, and a thickness of the filter element is compressed at the gripper to be 0.05 to 0.5 times the thickness.

According to this, the fitting step of closing the molds and fitting the inlet-side container element and the outlet-side container element is provided, thereby allowing the inlet-side container element and the outlet-side container element to be pressed against each other by a strong force. Consequently, the filter element can be compressed by the gripper to have a high density, such that the filter element is compressed to 0.05 to 0.5 times the thickness. As a result, the side leakage (side flow) where undesirable components flow over the outer edge portion of the filter element without being filtered can be effectively prevented. Consequently, the region of the outer edge portion compressed by the gripper can be facilitated to be reduced. Therefore, the blood processing filter can be manufactured where the risk of incomplete removal of undesirable components can be easily prevented without reducing the blood treatment efficiency.

A method of manufacturing a blood processing filter according to the second aspect of the present invention is a method of manufacturing a blood processing filter for removing undesirable components from liquid containing a blood component or blood, the method comprising: an injection molding step of injection-molding an inlet-side container element using one mold, and an outlet-side container element using another mold; a inserting step of inserting a filter element into the inlet-side container element or the outlet-side container element; a fitting step of mold-fitting the molds, and fitting the inlet-side container element and the outlet-side container element to each other; and a bonding step of bonding the inlet-side container element and the outlet-side container element to each other with melt resin, wherein the filter element includes a pair of filtering surfaces, and an end surface along peripheries of the pair of the filtering surfaces, the inlet-side container element and the outlet-side container element are provided with a gripper that clamps and compresses an outer edge portion of the pair of filtering surfaces, at least one of the inlet-side container element and the outlet-side container element is provided with a rib on an inner surface, and a coefficient of variation value (CV value) of the thickness of the filter element is 6% or less.

According to this manufacturing method, the fitting step of closing the molds and fitting the inlet-side container element and the outlet-side container element is provided, thereby allowing the inlet-side container element and the outlet-side container element to be pressed against each other by a strong force. In the case where the difference in thickness among positions of the filter element is large during filtering blood and the like, the resistance of a thick portion that is a portion with a low bulk density is low, and the blood and the like pass only through thick portions of the filter element. Consequently, a lopsided flow easily occurs, which causes a risk that not the entire filter can be used. Unlike this, since the method of manufacturing the blood processing filter according to the second aspect sets the coefficient of variation value of the thickness of the filter element to 6% or less, the lopsided flow of blood and the like can be prevented, and the blood processing filter whose entire filter element can be effectively used can be manufactured.

Advantageous Effects of Invention

The blood processing filter and the blood processing filter manufacturing method according to the first aspect of the present invention can easily avoid the risk of incomplete removal of undesirable components without reducing the blood treatment efficiency. The blood processing filter and the blood processing filter manufacturing method according to the second aspect of the present invention can uniformly use the entire filter element.

DESCRIPTION OF EMBODIMENT

Figure 1:
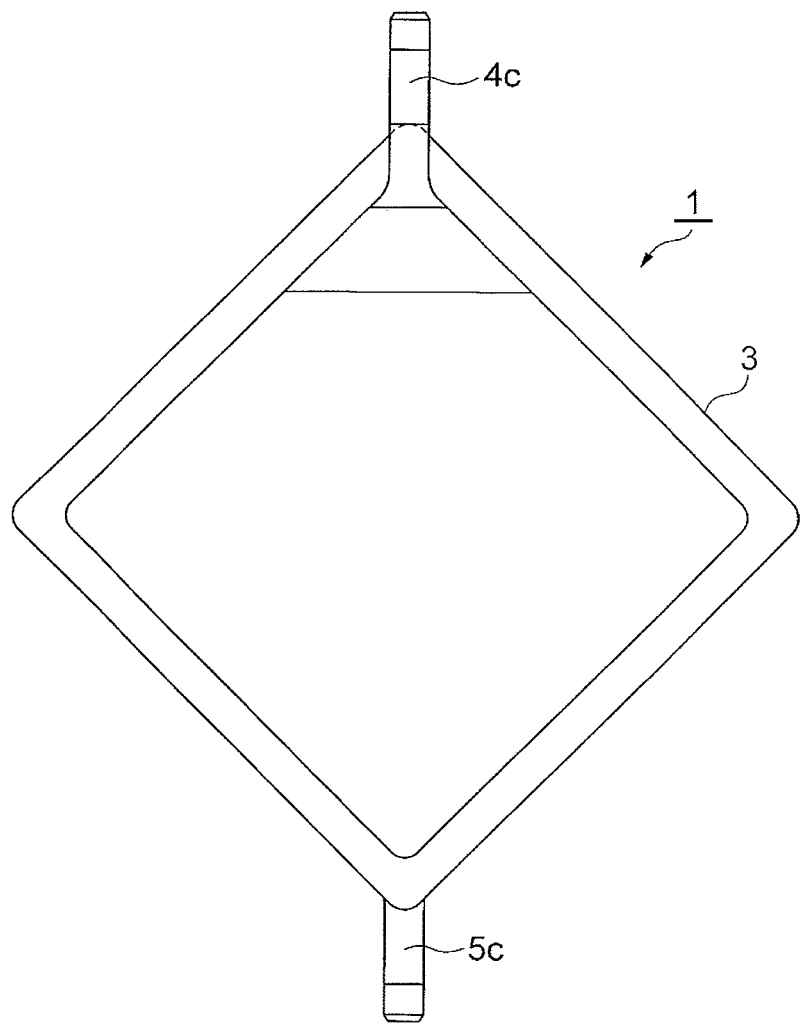
FIG. 1 is a top view of a blood processing filter according to an embodiment of the present invention.

Hereinafter, referring to the drawings, preferred embodiments of a blood processing filter and a blood processing filter manufacturing method according to the present invention are described in detail.

Figure 2:
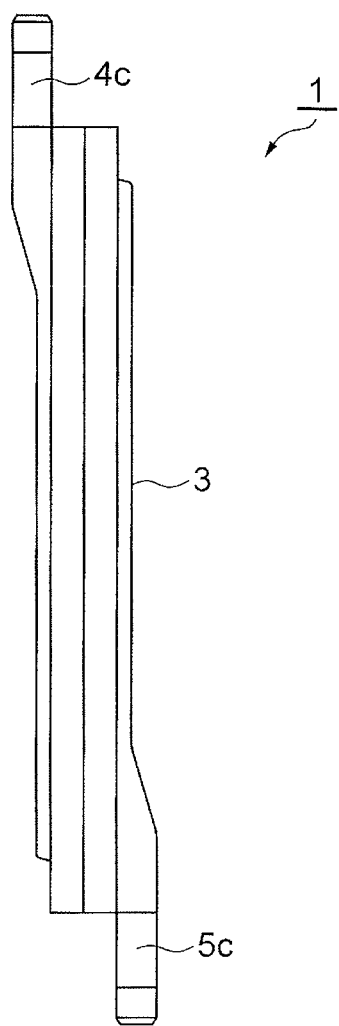
FIG. 2 is a side view of the blood processing filter according to the embodiment of the present invention.
Figure 3:
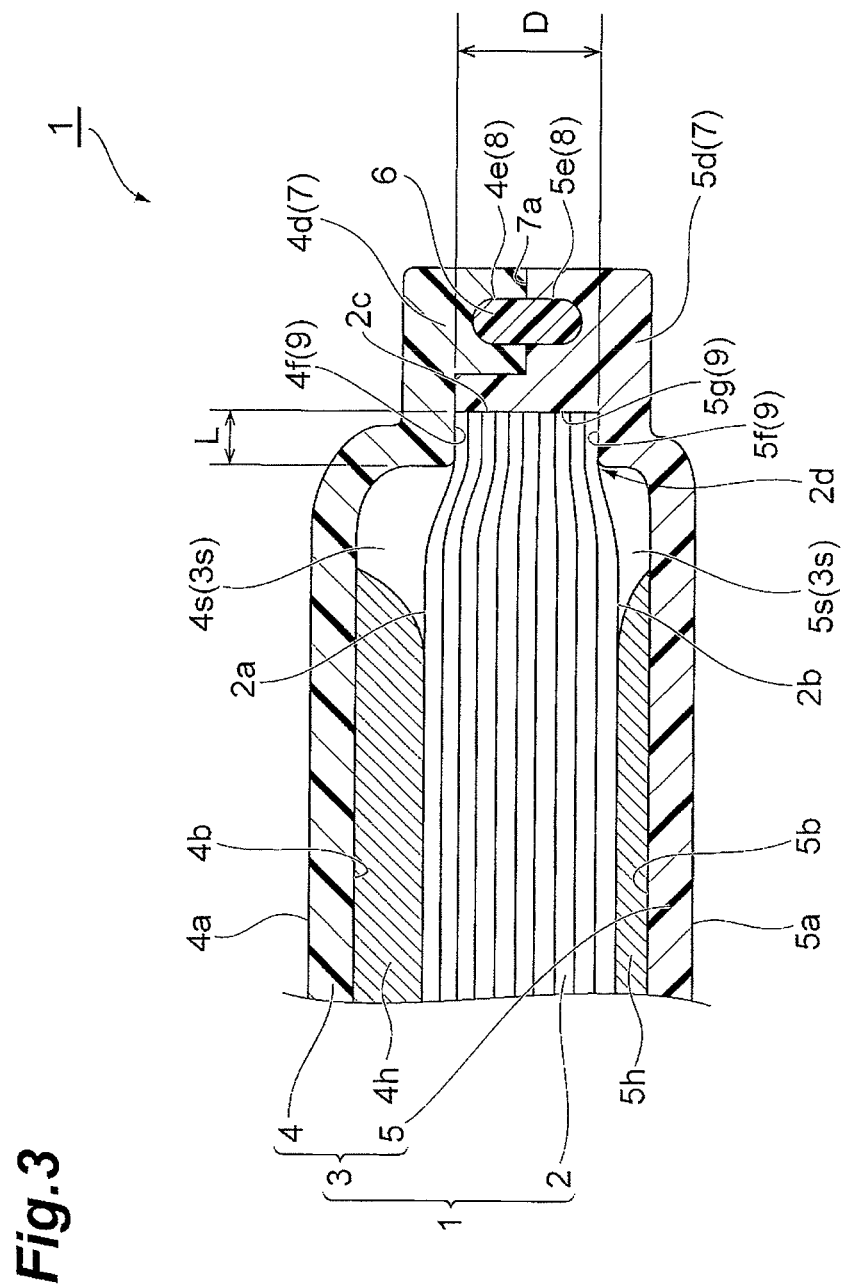
FIG. 3 is an enlarged sectional view of a gripper.

First, referring to FIGS. 1 to 3, a blood processing filter 1 relating to an embodiment is described. The blood processing filter 1 is for removing undesirable components from liquid containing blood components or blood (hereinafter, referred to as liquid to be treated). The blood processing filter 1 has a rectangular shape as a whole, and includes a sheet-shaped filter element 2 and a hard container 3. The hard container 3 includes an inlet-side container element 4 and an outlet-side container element 5 that are disposed to clamp the filter element 2. An internal space 3s is separated by the filter element 2 into an inlet space 4s and an outlet space 5s. Although the blood processing filter 1 may have any of a rectangular shape, a disk shape, an elliptic shape and the like, the rectangular shape is preferable to reduce the loss of material during manufacturing. A square shape and a rhombus are regarded as types of rectangular shapes.

The filter element 2 is a rectangular filter member that has a filtering surface 2a on the inlet space 4s side and a filtering surface 2b on the outlet space 5s side, and an end surface 2c along the peripheries of the pair of filtering surfaces 2a and 2b. The filter element 2 may be made of a well-known filtering medium, such as a fibrous and porous medium, e.g., nonwoven fabric, woven fabric or the like, or a porous body having three-dimensional continuous reticulate pores, e.g., spongiform structure. Examples of the materials include polypropylene, polyethylene, styrene-isobutylene-styrene copolymer, polyurethane, polyester and the like. The case where the filter element is made of nonwoven fabric is preferable particularly in view of productivity.

The filter element 2 may be a single filter element; or made of a plurality of filter elements. In the case where the element is made of a plurality of filter elements, it is preferred to include a first filter element that is disposed upstream and mainly removes microaggregates, and a second filter element that is disposed downstream of the first filter element for removing undesirable components other than microaggregates. For example, a filter material made of nonwoven fabric having fiber diameters ranging from several to several tens of micrometers is disposed on the inlet side as the first filter element for mainly removing aggregates, a filter material made of nonwoven fabric having fiber diameters ranging from 0.3 to 3.0 μm is disposed as the second filter element for removing other undesirable components, and a post filter having a specific shape on a further downstream side is stacked and used. Each of the first and second filter materials may be made of a plurality of types of filter materials. Alternatively, only one of these materials may be made of multiple filter materials. For example, a first filter material made of at least one of nonwoven fabric having fiber diameters ranging from 30 to 40 μm and nonwoven fabric having fiber diameters ranging from 10 to 20 μm may be disposed on the upstream side, and a second filter material made of at least one of nonwoven fabric having fiber diameters ranging from 1.5 to 2.5 μm and nonwoven fabric having fiber diameters ranging from 0.5 to 1.8 μm may be disposed on the downstream side of the first filter material, and these materials may be used. Alternatively, nonwoven fabric having large fiber diameters and nonwoven fabric having small fiber diameters may be alternately arranged. It is however preferred that the nonwoven fabric having large fiber diameters be arranged on the upstream side.

The hard container 3 is a rectangular container having a predetermined thickness, and includes the inlet-side container element 4 and the outlet-side container element 5 which are arranged to clamp the filter element 2. The internal space 3s of the hard container 3 is separated by the filter element 2 into the inlet space 4s and the outlet space 5s.

The inlet-side container element 4 is a rectangular member that is a cut of the hard container 3 having substantially half the thickness, and includes an outer surface 4a and an inner surface 4b. An inlet 4c is provided at one corner of the outer surface 4a. Meanwhile, the outlet-side container element 5 is a rectangular member that is the rest of the hard container 3, and includes an outer surface 5a and an inner surface 5b. An outlet 5c is provided at the corner of the outer surface 5a opposite to the corner provided with the inlet 4c. The inlet 4c and the outlet 5c are provided such that the inlet 4c protrudes upward and opens, and the outlet 5c protrudes downward and opens during use of the blood processing filter 1. An inlet-side fitting portion 4d and an outlet-side fitting portion 5d, which are elongated along the inner edge of the rectangular external shape and are fitted with each other, are provided on the inner surface 4b of the inlet-side container element 4 and the inner surface 5b of the outlet-side container element 5, respectively. The inlet-side fitting portion 4d and the outlet-side fitting portion 5d have a female and male relationship, and surround the end surface 2c of the filter element 2 and are fitted to each other to constitute a fitting portion 7.

At the fitting portion 7, a sliding surface 7a between the inlet-side fitting portion 4d and the outlet-side fitting portion 5d is provided with a resin flow path 8. The resin flow path 8 is a cavity made of a concave groove 4e and groove 5e provided at the inlet-side fitting portion 4d and the outlet-side fitting portion 5d, respectively. At least a part of the sliding surface 7a is bonded in a belt-shaped manner along the entire periphery of the fitting portion 7 by the inside of the resin flow path 8 being filled with melt resin 6. In this embodiment, both the groove 4e and the groove 5e are provided. Alternatively, only one of the grooves may be provided. The resin flow path 8 has a through-hole (not shown) that communicates with the outside of the hard container 3. The number of through-holes may be one or more. With such a belt-shaped bonding along the entire periphery of the fitting portion 7, the hard container 3 is sealed, which improves the airtightness and liquid-tightness. The through-hole is a hole through which the melt resin 6 is injected.

An inlet-side compression portion 4f and an outlet-side compression portion 5f are provided at the respective inner edges of the inlet-side fitting portion 4d and the outlet-side fitting portion 5d. The inlet-side compression portion 4f is made of a step of swelling of the inlet-side container element 4 on the inner surface 4b side. Likewise, the outlet-side compression portion 5f is made of a step of swelling of the outlet-side container element 5 on the inner surface 5b side. The inlet-side compression portion 4f and the outlet-side compression portion 5f clamp and compress the outer edge portion 2d of the pair of filtering surfaces 2a and 2b of the filter element 2. A close contact portion 5g that is in close contact with the end surface 2c of the filter element 2 is provided at the outer edge of the outlet-side compression portion 5f.

In this embodiment, the inlet-side compression portion 4f, the outlet-side compression portion 5f, and the close contact portion 5g constitute the gripper 9. The gripper 9 is positioned so as to be in close contact with the end surface 2c of the filter element 2 at the close contact portion 5g. Consequently, the gripper 9 is resistant to deviate, which is advantageous in high-density compression of the outer edge portion 2d of the pair of filtering surfaces 2a and 2b against each other. The gripper 9 allows the inlet-side compression portion 4f and the outlet-side compression portion 5f to compress an outermost edge of the filter element 2, that is, a range with a width L ranging from 1 to 5 mm from the position of the end surface 2c, the range being regarded as the outer edge portion 2d. Such a configuration with the gripper 9 having the width L more than 1 mm can prevent the filter element 2 from being apart from the gripper 9, and prevent insufficient removal from occurring, while the filter element 2 is pressed. The configuration where the width L of the gripper 9 incapable of being used for filtering in actuality is smaller than 5 mm facilitates design within a range allowable in view of blood treatment efficiency or economically.

A plurality of convex ribs 4h and 5h are further provided on inner sides of the inlet-side compression portion 4f and the outlet-side compression portion 5f on the inner surface 4b side of the inlet-side container element 4 and the inner surface 5b side of the outlet-side container element 5. The rib 4h is pressed against the filtering surface 2a of the filter element 2, and secures the inlet space 4s between the filtering surface 2a and the inner surface 4b of the inlet-side container element 4. Likewise, the rib 5h is pressed against the filtering surface 2b of the filter element 2, and secures the outlet space 5s between the filtering surface 2b and the inner surface 5b of the outlet-side container element 5. Thus, the filter element 2 is in a state where the pair of filtering surfaces 2a and 2b are clamped by the ribs 4h and 5h and thus compressed. The rib 4h is higher than the rib 5h, and the inlet space 4s is secured wider than the outlet space 5s. The heights of the ribs 4h and 5h may be the same. Alternatively, the rib 5h may be higher than the rib 4h.

The thickness D of the filter element 2 at the gripper 9 is required to be compressed to be 0.05 to 0.5 times as thick as the original thickness $D_0$, and $D/D_0=0.05$ to 0.5. Here, since the filter element cannot be compressed to have a density less than that of the original resin, in actuality it is difficult to achieve that smaller than $D/D_0=0.05$. On the other hand, if it is larger than $D/D_0=0.5$, the filter element cannot be regarded as being in a compressed state with a high density. A risk occurs that undesirable components flow over the outer edge portion of the filter element, resulting in a side leakage (side flow). Consequently, the performance of removing undesirable components, such as leukocytes, decreases. That is, it is important to have the filter element 2 with the thickness D, which is achieved by compressing the element to have a density close to the density of the original resin. As a result, the performance of removing undesirable components, such as leukocytes, can be improved. Thus, for example, in the case where the original thickness $D_0$ of the filter element 2 is 10 mm, it is required to compress the gripper 9 to have a thickness D of about 0.5 to 5 mm. In order to compress the gripper 9 to have the thickness D that is 0.05 to 0.5 times as thick as the original thickness $D_0$, the molding die is adjusted such that the distance of the gripper 9, that is, the distance between the opposite surfaces of the inlet-side compression portion 4f and the outlet-side compression portion 5f should be a thickness that is 0.05 to 0.5 times as thick as the original thickness $D_0$. In view of compatibility between easy manufacturability and performance of removing undesirable components, such as leukocytes, it is preferred that $D/D_0=0.07$ to 0.45, and it is further preferred that $D/D_0=0.1$ to 0.4.

Next, the original thickness $D_0$ of the filter element 2 in the case of verification of the blood processing filter 1 after molding is described. When the blood processing filter 1 after molding is taken apart and the thickness of a portion which is not clamped is measured; the maximum value $D_1$ of the thickness is a value with an error range, which is several percent, with reference to the original thickness $D_0$ before clamping by the gripper 9, and the maximum value $D_1$ can be substantially regarded as the original thickness $D_0$. More specifically, the maximum value $D_1$ is the maximum value of the thicknesses at five points selected from portions which are other than portions of the filter element 2 deformed by the convexes in the hard container 3, such as the gripper 9 and the rib 4h and the rib 5h, and is at and around the center of the filter element 2 and does not have a concave or the like, and has an unchanged form. The maximum value $D_1$ can be regarded as the original thickness $D_0$ before clamping by the gripper 9.

Figure 4:
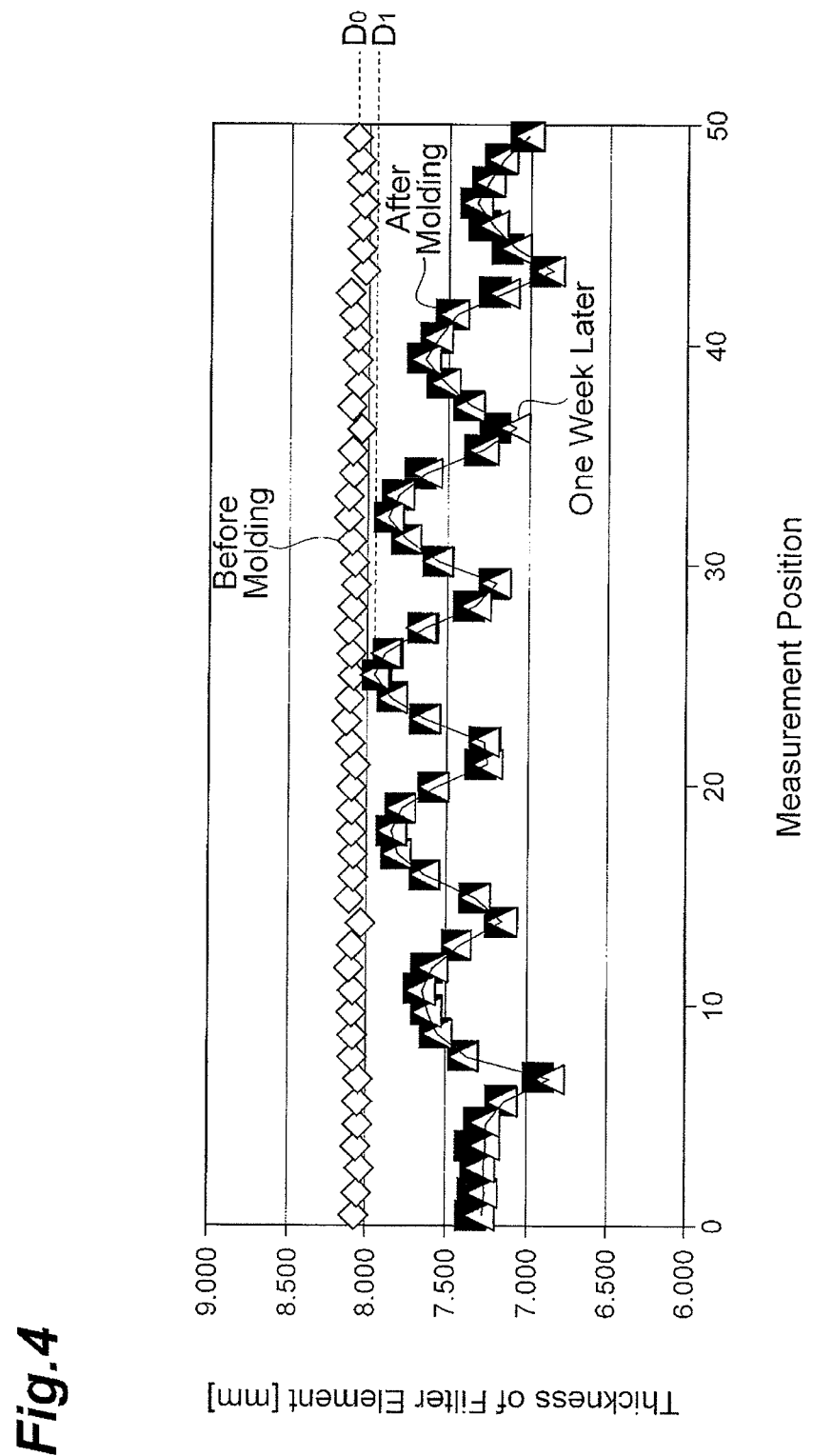
FIG. 4 shows a measurement result of measurement on the thickness of a filter element before and after molding.

An experimental result supporting this verification is described with reference to FIG. 4. FIG. 4 is a graph comparing the thickness of a section of the filter element 2 (polyester nonwoven fabric manufactured by Asahi Kasei Fibers Corporation) before molding of the blood processing filter 1 and after molding thereof (the blood processing filter 1 after molding is taken apart). As shown in FIG. 4, in the case of this blood processing filter 1, the difference between the original thickness $D_0$ and the maximum value $D_1$ is approximately 3% of the original thickness $D_0$. That is, it can be verified that the difference between the original thickness $D_0$ of the filter element 2 and the maximum value $D_1$ of the filter element 2 obtained by taking apart the blood processing filter 1 after molding is approximately several percent of the original thickness $D_0$. As to the measurement time of the thickness after taking apart, even comparison between thickness measurement results immediately after taking apart and those having been left for one week after taking apart show little variation. Consequently, it is verified that time elapsed from taking apart to measurement has little effect on thickness measurement results.

According to the above results, in the case where it is easier to detect the maximum value $D_1$ of the filter element 2 obtained by taking apart the blood processing filter 1 after molding than to grasp the original thickness $D_0$ before molding, the value of $D/D_0$ can be grasped by detecting the maximum value $D_1$ instead of the thickness $D_0$ and regarding the maximum value $D_1$ as the original thickness $D_0$. More specifically, $D_1$ should be equal to $D_0$ or smaller by several percent (i.e., $D_0 \geq D_1$). Consequently, when the thickness D is 0.5 times larger than the maximum value $D_1$ or less (i.e., $D/D_1 \leq 0.5$), the thickness D is equal to or smaller than a value that is 0.5 times as large as the original thickness $D_0$ (i.e., $D/D_0 \leq 0.5$). On the other hand, since the filter element 2 cannot be compressed to have a density that is equal to or smaller than the original resin, it is difficult to believe that the lower limit value is smaller than 0.05. Consequently, it is difficult to believe that the thickness D is smaller than 0.05 of the original thickness $D_0$ while the thickness D is 0.05 or larger than the maximum value $D_1$. That is, when $D/D_1=0.05$ to 0.5, it can be regarded that $D/D_0=0.05$ to 0.5.

The difference between the maximum value $D_1$ and the original thickness $D_0$ is approximately several percent of the original thickness $D_0$, and can thus be considered to be substantially ignored. However, even in the case of $D/D_1 > 0.5$, the error of several percent does not negate the possibility $D/D_0 \leq 0.5$ if $D_0$ can be actually detected.

Next, in the case of $D/D_0=0.07$ to 0.45 and the case of $D/D_0=0.1$ to 0.4 are described. The value of $D/D_0$ can physically be less than the lower limit values of 0.07 and 0.1. Thus, the lower limit value of $D/D_1$ at which the lower limit value of $D/D_0$ is securely 0.07 and 0.1 or more is discussed. Here, provided that the difference between the maximum value $D_1$ and the original thickness $D_0$ is a value, e.g., 10%, which is significantly larger than that in the above experiment (see FIG. 4), $D/D_1=0.078$ (=0.07/0.9) in the case of $D/D_0=0.07$, and $D/D_1=0.11$ (=0.1/0.9) in the case of $D/D_0=0.1$. That is, in the case of at least $D/D_1=0.078$ to 0.45, it is not improbable to regard $D/D_0=0.07$ to 0.45. In the case of $D/D_1=0.11$ to 0.4, it is not improbable to regard $D/D_0=0.1$ to 0.4.

Figure 8:
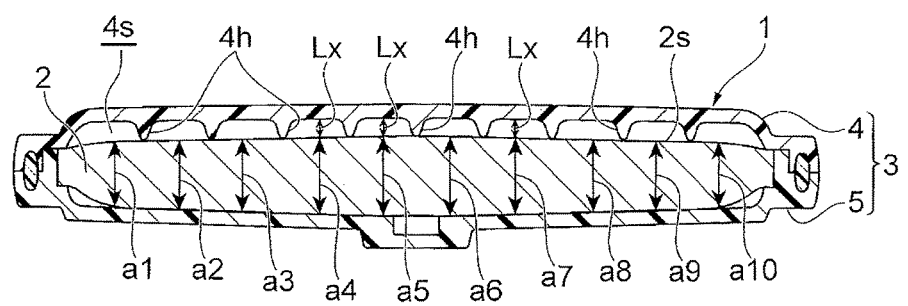
FIG. 8 is a sectional view of the blood processing filter for illustrating the coefficient of variation value (CV value) of the thickness of the filter element and the coefficient of variation value (CV value) of the distance from an inlet-side container element to an inlet-side surface of the filter element.

On the other hand, it is preferred that the coefficient of variation value (CV value) of the thickness of the filter element 2 be 6% or less. As shown in FIG. 8, the filter element 2 is fixed by the rib 4h provided to fix the filter element 2 at a predetermined position in the inlet space 4s and the outlet space 5s. However, since the element is compressed during fixation, the thickness is prone to be uneven. This is because, even if the repulsive force against compression during fixation is equivalent, deformation at the deformable center portion becomes large, and the thickness becomes uneven between the center portion and the peripheral portion. In particular, in the case of using the ultrasonic bonding method to bond the container, only the portion corresponding to the bonded portion of the container, i.e., the outermost periphery of the container, is pressed. Consequently, the thicknesses of the filter element at the central portion of the filter and the peripheral portion of the filter are prone to be uneven. Here, if the thicknesses of the filter element of the central portion of the filter and the peripheral portion of the filter are uneven, the unevenness causes lopsided flow, and possibility of problems. The lopsided flow is a phenomenon that blood selectively passes through a specific portion, and a portion without or resistant to the flow occurs.

In order to solve the above problems, in the blood processing filter 1 according to this embodiment, the thicknesses (a1, a2, . . . a10) of the filter element 2 are measured on at least three points between the rib 4h and the rib 4h and between the rib 4h and the peripheral portion, and the coefficient of variation value (CV value), which is the division of the standard deviation by the average value, is set to 6% or less. As a result, the lopsided flow can be prevented, and the blood processing filter 1 where the entire filter element 2 can be effectively used can be achieved. Here, the thickness of the filter element 2 may be measured on at least three points. It is preferred that the number of points be at least five, and between all the ribs 4h and the ribs 4h and between the ribs 4h and the peripheral portion be measured.

Furthermore, it is preferred that the coefficient of variation value (CV value) of the distance Lx from the inlet-side container element 4 to the inlet-side surface 2s of the filter element 2 in the inlet space 4s be 10% or less. As shown in FIG. 8, the filter element 2 is fixed by the rib 4h provided to fix the filter element 2 at a predetermined position in the inlet space 4s and the outlet space 5s. However, the filter element 2 is compressed during fixation, and the thickness is prone to be uneven. Consequently, the distance between the inlet-side container element 4 and the inlet-side surface 2s of the filter element 2 is also prone to be uneven. In particular, in the case of using the ultrasonic bonding to bond the container, only the portion corresponding to the bonded portion of the container, i.e., the periphery of the container, is pressed. Consequently, the thicknesses of the filter element 2 at the central portion of the filter and the peripheral portion of the filter are prone to be uneven.

In order to solve the above problems, in the blood processing filter 1 according to this embodiment, the distance Lx from the inlet-side container element 4 and the inlet-side surface 2s of the filter element 2 in the inlet space 4s is measured, corresponding to the portions measured as the thickness of the filter element 2 between the rib 4h and the rib 4h and between the rib 4h and the peripheral portion, and the coefficient of variation value (CV value), which is the division of the standard deviation by the average value, is set to 10% or less. As a result, blood and the like entering from the inlet evenly spreads into the inlet space 4s, and the filter element 2 can be effectively used.

In order to prevent deformation during filtering, it is preferred that the material of the hard container 3 be a resin having a Young's modulus of at least 1 GPa at room temperature, and it is further preferred that the material be a resin having a Young's modulus of at least 2 GPa. For example, polycarbonate, polyester, polyamide, polystyrene, HIPS, ABS, polyethylene, polypropylene, polyvinyl chloride or the like may be used. Heat-resistant polycarbonate, polyester, polyamide or the like is further preferable. As to measurement of Young's modulus, a result of measurement according to ISO527-1 can be used.

Figure 5:
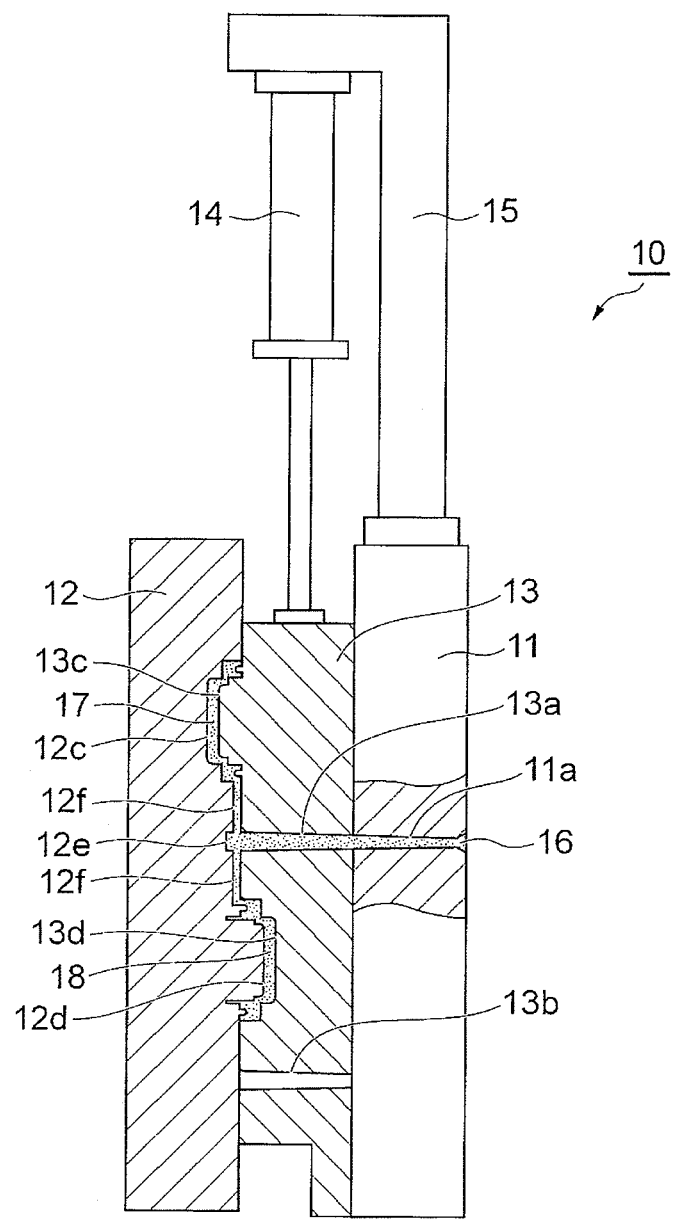
FIG. 5 is an illustration diagram for illustrating an injection molding step in manufacturing the blood processing filter according to the embodiment.

Next, an example of a method for manufacturing the blood processing filter 1 is described. As shown in FIG. 5, the injection molding machine 10 includes a fixed die 11, a movable die (mold) 12, and a slidable die (mold) 13. The fixed die 11 is fixed to a fixed platen (not shown) of the injection molding machine 10. A platform 15 that includes a cylinder 14 for sliding is provided on the upper surface of the fixed die 11. The cylinder 14 that is hydraulically or pneumatically moved is coupled onto the upper surface of the slidable die 13. The slidable die 13 is configured so as to be slidable and movable in a vertical direction while the state of being in close contact with a side surface of the fixed die 11 is kept.

The movable die 12 is attached to a movable platen (not shown) that is horizontally movable with respect to the injection molding machine 10. The movable platen is configured to be movable in a manner of approaching and being apart from the fixed die 11 by a mold opening and closing device (not shown) of the injection molding machine 10. The movable die 12 is configured to be movable between a mold closing position of being in close contact with the slidable die 13, and a mold opening position of being apart from the slidable die 13.

The fixed die 11 is provided, at its center, with a sprue 11a for guiding melt resin 16 injected from an injector (not shown) attached to the fixed die 11. The slidable die 13 is provided with a central sub-sprue 13a that continuously communicates with the sprue 11a when the die is at a lower position, and with a lower sub-sprue 13b that continuously communicates with the sprue 11a when the die is at an upper position.

A mold closing surface of the slidable die 13 is provided with a male mold 13c and a female mold 13d at vertically symmetric positions with respect to the central sub-sprue 12a. The male mold 13c is for molding the inner surface 4b of the inlet-side container element 4, and the female mold 13d is for molding the outer surface 5a of the outlet-side container element 5. On the other hand, a mold closing surface of the movable die 12 is provided with a female mold 12c and a male mold 12d facing the respective male mold 13c and female mold 13d when the slidable die 13 is at the lower position. The female mold 12c is for molding the outer surface 4a of the inlet-side container element 4, and the male mold 12d is for molding the inner surface 5b of the outlet-side container element 5. As in FIGS. 6 and 7, the female mold 12c on the movable die 12 side is configured to face the female mold 13d on the slidable die 13 side when the slidable die is at the upper position.

Figure 7:
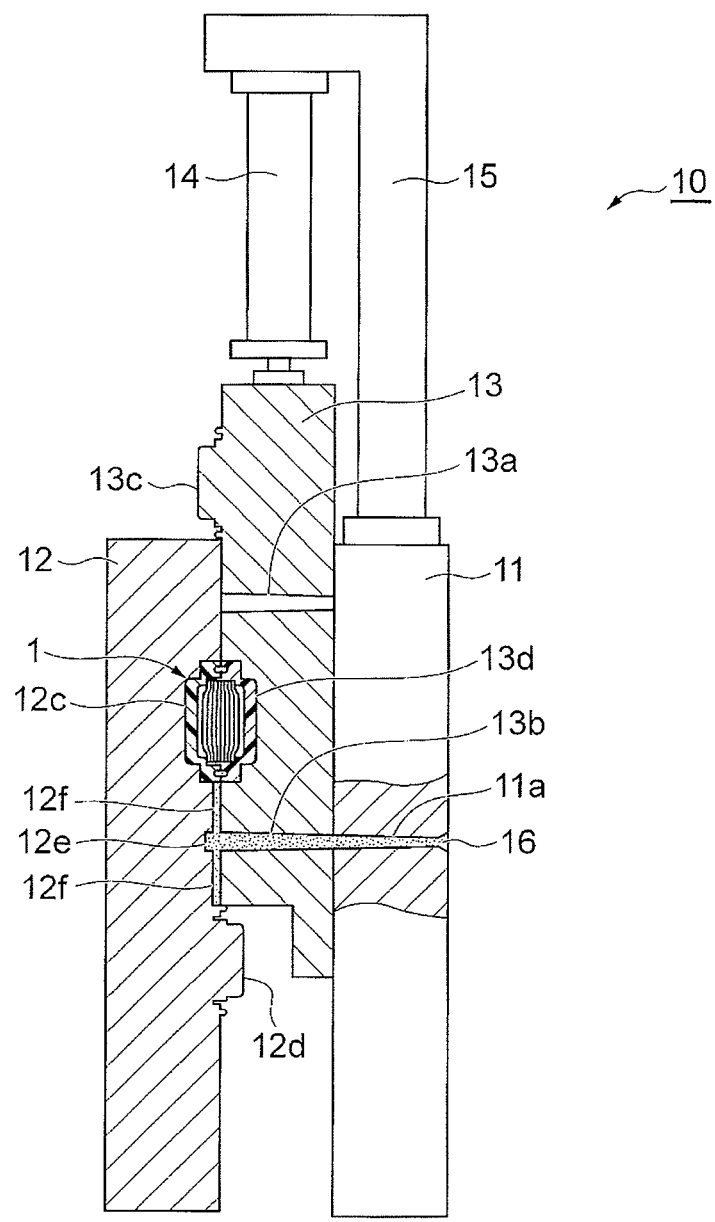
FIG. 7 is an illustration diagram for illustrating a fitting step in manufacturing the blood processing filter according to the embodiment of the present invention.

As shown in FIG. 5, when the slidable die 13 is at the lower position and the movable die 12 is mold-closed therewith, a pair of gaps 17 and 18 surrounded respectively by the male molds 12d and 13c and the female mold 13d and 12c are formed between the slidable die 13 and the movable die 12. At this time, the central sub-sprue 13a of the slidable die 13 is configured to communicate with these gaps through a runner 12e formed from the edge portions of the female molds 13d and 12c at the movable die 12 and through a runner 12e and a pair of gates 12f. As shown in FIG. 7, when the slidable die 13 is at the upper position and the movable die 12 is mold-fit therewith, the female molds 13d and 12c of the slidable die 13 and the movable die 12 fit with each other, and the lower sub-sprue 13b and the runner 12e communicate with the edge portions of these female molds 13d and 12c through the gates 12f.

In order to mold the blood processing filter 1 using such an injection molding machine 10, first, as shown in FIG. 5, the cylinder 14 is elongated to place the slidable die 13 at the lower position. Then, the movable platen of the injection molding machine 10 is moved on the fixed platen side, and mold-closes the slidable die 13 and the movable die 12. In this state, as shown in FIG. 5, the central sub-sprue 13a of the slidable die 13 communicates with the sprue 11a of the fixed die 11, and the pair of gaps 17 and 18 is formed between the slidable die 13 and the movable die 12. Next, the melt resin 16 is injected from the injector attached to the fixed platen, and the melt resin 16 is guided to both the gaps 17 and 18 through the sprue 11a of the fixed die 11, the central sub-sprue 13a of the slidable die 13, the runner 12e, and the gates 12f, and these gaps 17 and 18 are filled therewith. Thus, the male and female pair of inlet-side container element 4 and outlet-side container element 5 is formed in the respective gaps 17 and 18 (injection molding step).

Figure 6:
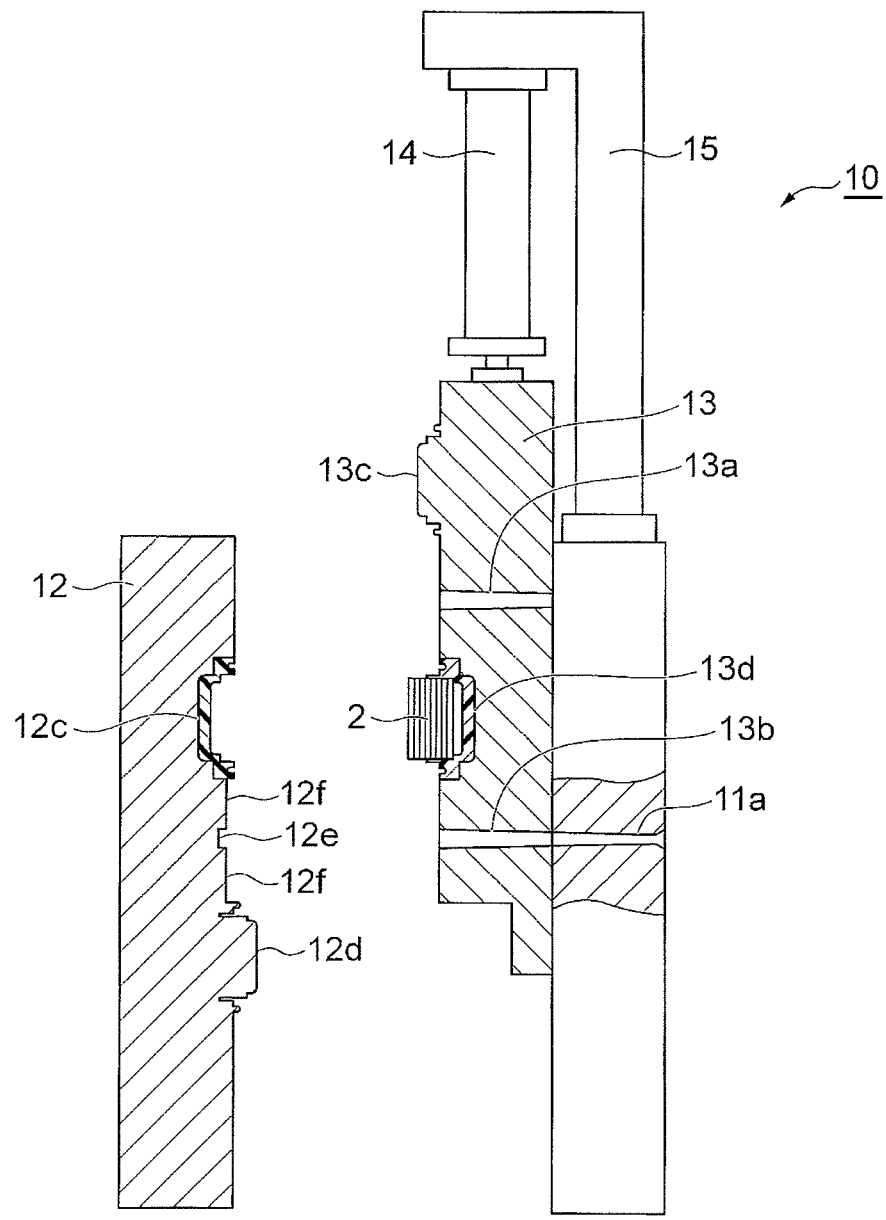
FIG. 6 is an illustration diagram for illustrating a inserting step in manufacturing the blood processing filter according to the embodiment.

After the male and female pair of inlet-side container element 4 and outlet-side container element 5 is cooled and solidified, the movable die 12 and the slidable die 13 are mold-opened by the mold opening and closing device and separated as shown in FIG. 6. Then, the male molds 13c and 12d are separated from the inlet-side container element 4 and the outlet-side container element 5, and the inlet-side container element 4 and the outlet-side container element 5 are left on the female molds 12c and 13s. In the mold opening, the resin portions solidified in the sprue 11a, the sub-sprue 13a, the runner 12e, the gates 12f and the like of the molds are pushed out of and dropped from the molds. The thus obtained inlet-side container element 4 and outlet-side container element 5 are provided with the inlet-side fitting portion 4d and the outlet-side fitting portion 5d, which are brought into contact with each other to form the fitting portion 7, along the inner edge of the rectangular external shape.

Next, the filter element 2 made of polyester nonwoven fabric is inserted into the outlet-side container element 5, and subsequently the cylinder 14 is retracted to move the slidable die 13 to the upper position (inserting step). Then, the female mold 13d of the slidable die 13 and the female mold 12c of the movable die 12 face with each other, the inlet-side container element 4 and the outlet-side container element 5 left on the female molds 13d and 12c are brought into a state of facing each other. At this time, the lower sub-sprue 13b of the slidable die 13 is placed so as to communicate with the sprue 11a of the fixed die 11. In this embodiment, the example where the filter element 2 is inserted in the outlet-side container element 5 is described. Alternatively, an exemplary example where the filter element 2 is inserted in the inlet-side container element 4 may be adopted.

In this state, the movable die 12 is moved toward the slidable die 13, and these dies are brought into contact and mold-fit with each other, as shown in FIG. 7, thereby fitting the inlet-side container element 4 and the outlet-side container element 5 with each other (fitting step). Thus; the fitting surfaces of the inlet-side fitting portion 4d and the outlet-side fitting portion 5d are fit with each other to form the resin flow path 8, which includes the groove 4e and the groove 5e, on the sliding surface 7a. The resin flow path 8 has a through-hole, and communicates with the gate 12f through the through-hole. The gate 12f, in turn, communicates with the sub-sprue 13b through the runner 12e. Consequently, when the melt resin 6 is injected as melt resin 16 from the injector in this state, the melt resin 6 passes through the sprue 11a of the fixed die 11, the sub-sprue 13b, the runner 12e, the gate 12f and the through-hole, and the resin flow path 8 is filled with the resin. Thus, the inlet-side container element 4 and the outlet-side container element 5 are bonded to each other at the periphery of the fitting portion 7 with the melt resin 6 (bonding step). As described above, according to the method of filling with the melt resin 6 after formation of the resin flow path 8, control of the amount of resin is facilitated.

The slidable die 13 and the movable die 12 are mold-opened again by the mold opening and closing device after the melt resin 6 is cooled and solidified, and the inlet-side container element 4 and the outlet-side container element 5 are fit and bonded to each other, and thus the blood processing filter 1, which is finished as a completely sealed molded product, is obtained. The resin portions solidified in the sprue 11a, the sub-sprue 13b, the runner 12e, the gates 12f and the like are pushed out of and dropped from the molds.

After the thus completed blood processing filter 1 is taken out, the cylinder 14 is elongated again to place the slidable die 13 at the lower position. Then, the movable die 12 and the slidable die 13 are mold-closed, and transition is made to a molding step for the next product. The series of steps as described above is repeated, thereby allowing the blood processing filters 1 to be successively molded. Furthermore, the molding step includes vertical sliding of the slidable die 13, mold-closing and mold-opening through forward and backward movement of the movable die 12, and injection of the melt resin 16, which are simple steps. Consequently, all the steps can be easily automated. Therefore, the blood processing filter 1 can be mass-produced.

Thus, only through use of a set of molds 12 and 13 and the injection molding machine 10, processes from injection molding of the inlet-side container element 4 and the outlet-side container element 5, and internal inserting of the filter element 2, and to bonding of the inlet-side container element 4 and the outlet-side container element 5, which are female and male container elements, can be consecutively performed in a single step, and even what is completely sealed can be molded.

The blood processing filter 1 manufactured by the above manufacturing method comprises: the sheet-shaped filter element 2; and the hard container 3 that includes the inlet-side container element 4 and the outlet-side container element 5 that are disposed to clamp the filter element 2, and has the internal space 3s separated by the filter element 2 into the inlet space 4s and the outlet space 5s, wherein the filter element 2 includes the filtering surface 2a on the inlet space 4s side, the filtering surface 2b on the outlet space 5s side, and the end surface 2c along the peripheries of the pair of filtering surfaces 2a and 2b, the inlet-side container element 4 and the outlet-side container element 5 are provided with the gripper 9 that clamps and compresses the outer edge portion 2d of the pair of filtering surfaces 2a and 2b, and the thickness D of the filter element 2 is compressed by the gripper 9 to be 0.05 to 0.5 times the thickness.

The blood processing filter 1 can prevent a side leakage (side flow) where undesirable components flow over the outer edge portion 2d of the filter element 2 without being filtered, by the gripper 9 that compresses the filter element 2 to have a thickness D that is 0.05 to 0.5 times the thickness. As a result, the region of the outer edge portion 2d compressed by the gripper 9 can be facilitated to be reduced. Consequently, the risk of incomplete removal of undesirable components can be easily avoided without reducing the blood treatment efficiency.

Furthermore, the gripper 9 of the blood processing filter 1 is positioned so as to be in close contact with the end surface 2c. Consequently, the gripper 9 is resistant to deviate, which is advantageous in high-density compression of the outer edge portion 2d of the pair of filtering surfaces 2a and 2b against each other.

Furthermore, in the blood processing filter 1, since the gripper 9 compresses the range with a width L ranging from 1 to 5 mm from the outermost edge of the filter element 2 as the outer edge portion 2d, the filter element 2 can be prevented from being separated from the gripper 9, and design within a range allowable in view of blood treatment efficiency or economically is facilitated.

Furthermore, in the blood processing filter 1, the inlet-side container element 4 and the outlet-side container element 5 further include the fitting portion 7 that surrounds the end surface 2c of the filter element 2 and is fitted, thereby facilitating positioning and joining of the inlet-side container element 4 and the outlet-side container element 5.

Furthermore, in the blood processing filter 1, the fitting portion 7 includes the inlet-side fitting portion 4d provided at the inlet-side container element 4, and the outlet-side fitting portion 5d provided at the outlet-side container element 5, and at least a part of the sliding surface 7a between the inlet-side fitting portion 4d and the outlet-side fitting portion 5d is bonded in a belt shaped manner along the entire periphery of the fitting portion 7 with the melt resin 6. Consequently, the airtightness and liquid-tightness are high.

Furthermore, in the blood processing filter 1, the sliding surface 7a is provided with the resin flow path 8, and the inside of the resin flow path 8 is filled with the melt resin 6 to bond the sliding surface 7a. Consequently, the melt resin 6 is resistant to protruding from the sliding surface 7a, and there is no possibility of intrusion into the hard container 3.

Furthermore, in the blood processing filter 1, the hard container 3 is made of resin with a Young's modulus of at least 1 GPa at room temperature, which can prevent deformation during filtering.

In the blood processing filter 1, the rib 4h and the rib 5h are provided on the inner surfaces of the inlet-side container element 4 and the outlet-side container element 5, and the coefficient of variation value (CV value) of the thickness of the filter element 2 is 6% or less. As a result, the lopsided flow of blood or the like is prevented, and the entire filter element can be effectively utilized. In this embodiment, the example of the case is described where the rib 4h and the rib 5h are provided at both the inlet-side container element 4 and the outlet-side container element 5. Alternatively, the case where the rib 4h and the rib 5h are provided at one of the inlet-side container element 4 and the outlet-side container element 5 is the same.

In the blond processing filter 1, the rib 4h is provided on the inner surface of the inlet-side container element 4, and the coefficient of variation value (CV value) of the distance Lx from the inlet-side container element 4 to the inlet-side surface 2s of the filter element 2 in the inlet space 4s is 10% or less. As a result, blood and the like entering from the inlet evenly spreads into the inlet space 4s, and the filter element 2 can be effectively used.

The method of manufacturing the blood processing filter 1 according to this embodiment comprises: an injection molding step of injection-molding the inlet-side container element 4 using the male mold 13c of the slidable die 13 and the female mold 12c of the movable die 12, and the outlet-side container element 5 using the female mold 13d of the slidable die 13 and the male mold 12d of the movable die 12; a inserting step of inserting the filter element 2 into the inlet-side container element 4 or the outlet-side container element 5; a fitting step of mold-closing the movable die. 12 and the slidable die, 13 that are a set of molds, and fitting the inlet-side container element 4 and the outlet-side container element 5 to each other; and a bonding step of bonding the inlet-side container element 4 and the outlet-side container element 5 to each other with melt resin 6, wherein the filter element 2 includes the pair of filtering surfaces 2a and 2b, and the end surface 2c along the peripheries of the pair of the filtering surfaces 2a and 2b, the inlet-side container element 4 and the outlet-side container element 5 are provided with the gripper 9 that clamps and compresses outer edge portion 2d of the pair of filtering surfaces 2a and 2b, and the thickness D of the filter element 2 is compressed at the gripper 9 to be 0.05 to 0.5 times the thickness.

According to this, the fitting step of mold-closing the movable die 12 and the slidable die 13 and fitting the inlet-side container element 4 and the outlet-side container element 5 is provided, thereby allowing the inlet-side container element 4 and the outlet-side container element 5 to be pressed against each other by a strong force of, e.g., several tf (ton-force). Note that in ultrasonic bonding; the force is several hundreds of kgf (kilogram-force). Consequently, a side leakage (side flow) where undesirable components flow over the outer edge portion 2d of the filter element 2 without being filtered can be prevented by the gripper 9 that is in close contact with the end surface 2c of the filter element 2 and compresses the filter element 2 to have the thickness D that is 0.05 to 0.5 times the thickness. As a result, the region of the outer edge portion 2d compressed by the gripper 9 can be facilitated to be reduced. Consequently, the risk of incomplete removal of undesirable components can be easily prevented without reducing the blood treatment efficiency.

Furthermore, in the manufacturing method according to this embodiment, the gripper 9 is positioned so as to be in close contact with the end surface 2c. Consequently, the gripper 9 is resistant to deviate, which is advantageous in high-density compression of the outer edge portion 2d of the pair of filtering surfaces 2a and 2b against each other.

In the case where the difference in thickness among positions of the filter element is large during filtering of blood and the like, the resistance of a portion with a low bulk density is low, and the blood and the like pass only through thick portions of the filter element. Consequently, a lopsided flow easily occurs, which causes a risk that not the entire filter element can be used. Unlike this, since the aforementioned manufacturing method sets the coefficient of variation value of the thickness of the filter element to 6% or less, the method can prevent the lopsided flow of blood and the like, and manufacture the blood processing filter whose entire filter element can be effectively used.

Although the present invention has thus been described with reference to the embodiments, the present invention is not limited to the embodiments. For example, the inlet-side container element 4 and the outlet-side container element 5 may be fitted to each other, and subsequently the hard container 3 and the filter element 2 may be integrally bonded to each other using high frequency bonding to thereby obtain the blood processing filter 1. Alternatively, after formation of the hard container 3, the resin flow path 8 may be filled with the melt resin 6 in a different method to thereby obtain the blood processing filter 1. Examples of the different method include a method of mounting the filter element 2, and preliminarily providing the melt resin 6 for at least one of the groove 4e and the groove 5e, which are to be the resin flow path 8, and then performing mold closing.

Note that in order to prevent occurrence of side leakage where liquid to be treated flows over the outer edge portion 2d of the filter element 2 without being filtered, it is effective to configure, higher, the density of the filter element 2 that is to be compressed, which is as described above. However, in the case of ultrasonic bonding typically used for container bonding, it is difficult to compress the filter element to have a high density. Even in the compressible case, leakage at a bonded portion of the bonded blood processing filter occurs, and a crack or the like occurs due to excessive pressing of the containers to each other.

The inlet-side container element 4 and the outlet-side container element 5 may be those that do not include the inlet-side fitting portion 4d and the outlet-side fitting portion 5d, but include an inlet-side contact portion (not shown) and an outlet-side fitting portion (not shown) where the sliding surface 7a forms a single plane. That is, the inlet-side container element 4 and the outlet-side container element 5 may not have a male-female relationship.

EXAMPLES

The present invention will now be described in further detail below by way of examples. However, the present invention is not limited to these examples.
(Filtering Performance Evaluation on Whole Blood)

A whole blood preparation adjusted as follows was used for filtering performance evaluation. 2100 mL of pig whole blood was collected and mixed into a blood bag containing 320 mL of anticoagulant CPD, and relatively coarse aggregates generated during blood collection were removed by filtering with a preprocess filter other than the blood processing filters of Examples and Comparative Examples, which will be described later. The preprocess filter has a configuration where twelve sheets with an average value of pore diameters of 60 μm and a weight per unit area of 50 g/m², eight sheets with an average value of pore diameters of 50 μm and a weight per unit area of g/m², and eight sheets with an average value of pore diameters of 50 μm and a weight per unit area of 30 g/m² are stacked from the upstream side in this order, and accommodated in a container made of rigid resin with a filtering area of 45 cm². The blood from which the coarse aggregates in blood collection had been removed by the pre-process filter was divided into 460 mL-portions and injected into respective bags on the day of blood collection. The thus obtained whole blood preparations were left at room temperature, and filtered with the blood filters of Examples and Comparative Examples at room temperature on the day of blood collection. The filtering time from the start of filtering to the end was measured, and adopted as the filtering time. The leukocyte removing performance was calculated by the following Equation (1).

leukocyte removing performance=Log (concentration of leukocyte before filtering (cells/μL)/concentration of leukocyte after filtering (cells/μL)) (1)

The concentrations of leukocyte before and after filtering were measured using an automatic blood cell analyzer SF3000 (Sysmex Corporation).

Experiment Example 1

Example 1

The blood processing filter according to Example 1 was created using the method described in the method of manufacturing the blood processing filter 1 according to the aforementioned embodiment. That is, the inlet-side container element was formed by the one mold and the outlet-side container element was formed by the other mold, and subsequently the blood processing filter element was inserted into the outlet-side container element, and the female and male inlet-side container element and outlet-side container element were brought into contact and fitted with each other by moving the mold. Subsequently, the blood processing filter was created using the method of injecting the melt resin through the flow path of the mold formed at the periphery of the fitting portion of the inlet-side container element and the outlet-side container element into the resin flow path of the hard container and of bonding the entire periphery of the fitting portion.

The material of the hard container was polycarbonate resin, the distance of the gripper, i.e., the thickness D of the filter element at the gripper was set to 3.6 mm, the width L of the gripper was set to 5 mm, and the effective filtering area was 46 cm². Furthermore, polyester nonwoven fabric was stacked according to the following configuration for use as the filter element. The original thickness $D_0$ of the filter element was 9.1 mm.
polyester nonwoven fabric 1 (the average fiber diameter is 12 μm, and the weight per unit area is 30 g/m²) 6 sheets
polyester nonwoven fabric 2 (the average fiber diameter is 1.6 μm, and the weight per unit area is 66 g/m²) 2 sheets
polyester nonwoven fabric 3 (the average fiber diameter is 1.2 μm, and the weight per unit area is 30 g/m²) 32 sheets The result of an experiment through use of the thus created blood processing filter is shown in Table 1. The leukocyte removing performance is 1.46, which shows high performance.

Example 2

The blood processing filter was created in a manner similar to that in Example 1 except that the distance of the gripper between the inlet-side container element and the outlet-side container element, i.e., the thickness D of the filter element at the gripper was set to 0.95 mm and the width L of the gripper was set to 1 mm. The result of an experiment through use of this blood processing filter is shown in Table 1. The leukocyte removing performance is 1.52, which shows high performance.

Example 3

The blood processing filter was created in a manner similar to that in Example 1 except that HIPS resin was adopted as the container material, the distance of the gripper, i.e., the thickness D of the filter element at the gripper was set to 0.95 mm and the width L of the gripper was set to 5 mm. The result of an experiment through use of this blood processing filter is shown in Table 1. The leukocyte removing performance is 1.44, which shows high performance.

Example 4

The blood processing filter was created in a manner similar to that in Example 1 except that the distance of the gripper, i.e., the thickness D of the filter element at the gripper was set to 3.6 mm and the width L of the gripper was set to 1 mm. The result of an experiment through use of this blood processing filter is shown in Table 1. The leukocyte removing performance is 1.47, which shows high performance.

Comparative Example 1

The blood processing filter was created in a manner similar to that in Example 1 except that the distance of the gripper, i.e., the thickness D of the filter element at the gripper was set to 5 mm and the width L of the gripper was set to 1 mm. The result of an experiment through use of this blood processing filter is shown in Table 1. The leukocyte removing performance was 0.50, which was lower than that in Examples 2 and 4. In other words, it was confirmed that even though the condition, such as the width L of the gripper, was the same, sufficient leukocyte removing performance could not be achieved with an insufficient compressibility ratio.

Comparative Example 2

The blood processing filter was created in a manner similar to that in Example 1 except that the distance of the gripper, i.e., the thickness D of the filter element at the gripper was set to 5 mm and the width L of the gripper was set to 5 mm. The result of an experiment through use of this blood processing filter is shown in Table 1. The leukocyte removing performance was 0.55, which is lower than that in Examples 1 and 3. In other words, it was confirmed that even though the condition, such as the width L of the gripper, was the same, sufficient leukocyte removing performance could not be achieved with an insufficient compressibility ratio.

TABLE 1

| | D (mm) | Compressibility Ratio (Factor) | L (mm) | Leukocyte Removing Performance (—) |
|---|---|---|---|---|
| Example 1 | 3.6 | 0.396 | 5 | 1.46 |
| Example 2 | 0.95 | 0.104 | 1 | 1.52 |
| Example 3 | 0.95 | 0.104 | 5 | 1.44 |
| Example 4 | 3.6 | 0.396 | 1 | 1.47 |
| Comparative Example 1 | 5 | 0.549 | 1 | 0.50 |
| Comparative Example 2 | 5 | 0.549 | 5 | 0.55 |

Experiment Example 2

Method of Measuring CV Value of Thickness of Filter Element

An image of a section of the blood processing filter was taken using X-ray CT. The section was selected so as to pass through the center portion where the thickness of the filter element was the maximum. For example, it was preferred to select the section so as to pass through the barycenter of the blood processing filter. In the case where ribs provided at the inlet-side container element or the outlet-side container element were linearly arranged, it was preferred to select the section so as to be perpendicular to the ribs. As to the ribs provided for at least one of the inlet-side container element and the outlet-side container element, at an intermediate point between the ribs and at an intermediate point between the rib and external periphery, the thicknesses ($a1, a2, \ldots, a10$) of the filter element were measured at at least three points (preferably at five points, and more preferably at ten points), and the CV value was calculated by dividing the standard deviation by the average value.

(Method of Measuring CV Value of Distance Between Inlet-Side Container Element and Inlet-Side Surface of Filter Element)

As to the ribs provided for at least one of the inlet-side container element and the outlet-side container element, at an intermediate point between the ribs and at an intermediate point between the rib and external periphery, the distance between the inlet-side container element and the inlet-side surface of the filter element was measured at at least three points (preferably at five points), and the CV value was calculated by dividing the standard deviation by the average value.

Example 5

The blood processing filter according to Example 5 was created using the method described in the method of manufacturing the blood processing filter 1 according to the aforementioned embodiment. That is, the inlet-side container element was formed by the one mold and the outlet-side container element was formed by the other mold, and subsequently the blood processing filter element was inserted into the outlet-side container element, and the female and male inlet-side container element and outlet-side container element were brought into contact and fitted with each other by moving the mold. Subsequently, the blood processing filter was created using the method of injecting the melt resin through the flow path of the mold formed at the periphery of the fitting portion of the inlet-side container element and the outlet-side container element into the resin flow path of the hard container and of bonding the entire periphery of the fitting portion.

Furthermore, a stack according to the following configuration was used as the filter element.

polyester nonwoven fabric 1 (the average fiber diameter is 12 μm, and the weight per unit area is 30 g/m$^2$) 6 sheets
polyester nonwoven fabric 2 (the average fiber diameter is 1.6 μm, and the weight per unit area is 66 g/m$^2$) 2 sheets
polyester nonwoven fabric 3 (the average fiber diameter is 1.2 μm, and the weight per unit area is 30 g/m$^2$) 32 sheets The material of the hard container was polycarbonate resin, the coefficient of variation value (CV value) of the thickness of the filter element was 5.9%, and the coefficient of variation value (CV value) of the distance between the inlet-side container element and the inlet-side surface of the filter element was 9.6%. Through use of the thus created blood processing filter, blood filtering was started, the time until the entire surface on the outlet side being evenly wet was measured and the result was shown in Table 2.

Example 6

Furthermore, a stack according to the following configuration was used as the filter element.

polyester nonwoven fabric 1 (the average fiber diameter is 12 μm, and the weight per unit area is 30 g/m²) 6 sheets
polyester nonwoven fabric 2 (the average fiber diameter is 1.6 μm, and the weight per unit area is 66 g/m²) 2 sheets
polyester nonwoven fabric 3 (the average fiber diameter is 1.2 μm, and the weight per unit area is 30 g/m²) 30 sheets The blood processing filter was created as with Example 1 except that the material of the hard container was polycarbonate resin, the CV value of the thickness of the filter element was 3.6%, and the CV value of the distance between the inlet-side container element and the inlet-side surface of the filter element was 10%. An experiment was performed using this blood processing filter, and the result is shown in Table 2.

Comparative Example 3

In Comparative Example 3, a blood processing filter was created using a method of forming the inlet-side container element and the outlet-side container element formed using the molds, subsequently installing the filter element, and bonding the container by ultrasonic bonding. In Comparative Example 3, the blood processing filter was created as with Example 1 except that the CV value of the thickness of the filter element was 6.7%, and the CV value of the distance between the inlet-side container element and the inlet-side surface of the filter element was 18%. Through use of this blood processing filter, blood filtering was started, the time until the entire surface on the outlet side being evenly wet was measured. The result is shown in Table 2.

Comparative Example 4

In Comparative Example 4, a blood processing filter was created using a method of forming the inlet-side container element and the outlet-side container element formed using the molds, subsequently installing the filter element, and bonding the container by ultrasonic bonding. In Comparative Example 4, the blood processing filter was created as with Example 1 except that the CV value of the thickness of the filter element was 6.7%, and the CV value of the distance between the inlet-side container element and the inlet-side surface of the filter element was 10%. Through use of this blood processing filter, blood filtering was started, the time until the entire surface on the outlet side being evenly wet was measured. The result is shown in Table 2.

Example 7

The blood processing filter was created as with Example 1 except that the CV value of the distance between the inlet-side container element and the inlet-side surface of the filter element was 18.6%. The result of an experiment through use of this blood processing filter is shown in Table 2.

Example 8

The blood processing filter was created as with Example 1 except that the CV value of the thickness of the filter element was 3.6%, and the CV value of the distance between the inlet-side container element and the inlet-side surface of the filter element was 18.6%. The result of an experiment through use of this blood processing filter is shown in Table 2.

TABLE 2

|  | CV Value of Thickness of Filter Element (%) | CV Value of Distance From Inlet Side Container element to Inlet-Side Surface of the Filter Element (%) | Time Until Entire Surface on Outlet Side Being Evenly wet (s) |
| --- | --- | --- | --- |
| Example 5 | 5.9 | 9.6 | 21 |
| Example 6 | 3.6 | 10 | 20 |
| Comparative Example 3 | 6.7 | 18.6 | 35 |
| Comparative Example 4 | 6.7 | 10 | 33 |
| Example 7 | 5.9 | 18.6 | 21 |
| Example 8 | 3.6 | 18.6 | 22 |

(General Result)

As shown in Table 2, in the case of each of the blood processing filters according to Example 5, Example 6, Example 7, and Example 8, the CV value (%) of the thickness of the filter element is 6% or less. In the case of the blood processing filters according to Comparative Examples 3 and 4, the CV value (%) of the thickness of the filter element exceeds 6%. In the case of each of the blood processing filters according to Example 5, Example 6, Example 7, and Example 8, the time for allowing the entire surface on the outlet side to get evenly wet was 20 to 22 seconds, which was short. On the other hand, in the cases of the blood processing filters according to Comparative Example 3 and Comparative Example 4, the time for allowing the entire surface on the outlet side to become evenly wet was 33 to 35 seconds, which were considerably long. In other words, according to Example 5, Example 6, Example 7 and Example 8, the time in which blood having entered from the inlet evenly spread is short. Accordingly, it can be demonstrated that the filter element can be effectively used in comparison with Comparative Examples 3 and 4.

In the case of each of the blood processing filters according to Example 5 and Example 6, the CV value of the distance between the inlet-side container element and the inlet-side surface of the filter element is 10% or less. Meanwhile, in the case of each of the blood processing filters according to Example 7 and Example 8, the CV value of the distance between the inlet-side container element and the inlet-side surface of the filter element exceeds 10%. In comparison between the blood processing filters according to Example 5 and Example 6 and the blood processing filters according to Example 7 and Example 8, there was a tendency that the blood processing filters according to Example 5 and Example 6 require slightly shorter time for making the entire surface on the outlet side be uniformly wet. That is, it can be estimated that the filter element of the case where the CV value of the distance between the inlet-side container element and the inlet-side surface of the filter element is 10% or less can be more effectively used.

REFERENCE SIGNS LIST

1 . . . Blood processing filter, 2 . . . Filter element, 2a, 2b . . . Filtering surface, 2c . . . End surface, 2d . . . Outer edge portion, 2s . . . Inlet-side surface, 3 . . . Hard container, 3s . . . Internal space, 4 . . . Inlet-side container element, 4a . . . Outer surface, 4b . . . Inner surface, 4c . . . Inlet, 4d . . . Inlet-side fitting portion, 4e . . . Groove, 4f . . . Inlet-side compression portion, 4h . . . Rib, 4s . . . Inlet space, 5 . . . Outlet-side container element, 5a . . . Outer surface, 5b . . . Inner surface, 5c . . . Outlet, 5d . . . Outlet-side fitting portion, 5e . . . Groove, 5f . . . Outlet-side compression portion, 5g . . . Close contact portion, 5h . . . Rib, 5s . . . Outlet space, 6 . . . Melt resin, 7 . . . Fitting portion, 7a . . . Sliding surface, 8 . . . Resin flow path, 9 . . . Gripper, 12 . . . Movable die, 13 . . . Slidable die, D . . . Thickness, L . . . Width.

The invention claimed is:

1. A blood processing filter for removing undesirable components from liquid containing a blood component or blood, the filter comprising:
  a sheet-shaped filter element; and
  a hard container that includes an inlet-side container element and an outlet-side container element that are disposed to clamp the filter element, and has an internal space separated by the filter element into an inlet space and an outlet space,
  wherein the filter element includes a filtering surface on a side of the inlet space, a filtering surface on a side of the outlet space, and an end surface along peripheries of the pair of filtering surfaces,
  the inlet-side container element and the outlet-side container element are provided with a gripper that clamps and compresses an outer edge portion of the pair of filtering surfaces,
  a thickness of the filter element is compressed by the gripper to be 0.05 to 0.5 times the thickness,
  at least one of the inlet-side container element and the outlet-side container element is provided with a rib on an inner surface, the rib being pressed against the filtering surface of the filter element, and
  a coefficient of variation value of the thickness of the filter element is 6% or less.

2. The blood processing filter according to claim 1, wherein the gripper compresses the filter element at a range with a width of 1 to 5 mm from an outermost edge, as the outer edge portion.

3. The blood processing filter according to claim 1, wherein a coefficient of variation value of a distance from the inlet-side container element to an inlet-side surface of the filter element in the inlet space is 10% or less.

4. The blood processing filter according to claim 1, wherein the gripper is in close contact with the end surface of the filter element.

5. The blood processing filter according to claim 1, wherein the inlet-side container element and the outlet-side container element further include a fitting part from fitting portions surrounding the end surface of the filter element and fitted to one another.

6. The blood processing filter according to claim 5, wherein the fitting portion includes an inlet-side fitting portion provided at the inlet-side container element, and an outlet-side fitting portion provided at the outlet-side container element, and
  at least a part of a sliding surface between the inlet-side fitting portion and the outlet-side fitting portion is bonded along an entire periphery of the fitting portion with melt resin.

7. The blood processing filter according to claim 6, wherein the sliding surface is provided with a resin flow path, the resin flow path is filled with the melt resin to bond the sliding surface.

8. The blood processing filter according to claim 1, wherein the hard container is made of resin with a Young's modulus of at least 1 GPa at room temperature.

9. A method of manufacturing a blood processing filter for removing undesirable components from liquid containing a blood component or blood, the method comprising:
  injection-molding an inlet-side container element using one mold, and an outlet-side container element using another mold;
  inserting a filter element into the inlet-side container element or the outlet-side container element;
  mold-fitting the molds, and fitting the inlet-side container element and the outlet-side container element to each other; and
  bonding the inlet-side container element and the outlet-side container element to each other with melt resin,
  wherein the filter element includes a pair of filtering surfaces, and an end surface along peripheries of the pair of the filtering surfaces,
  the inlet-side container element and the outlet-side container element are provided with a gripper that clamps and compresses an outer edge portion of the pair of filtering surfaces,
  a thickness of the filter element is compressed at the gripper to be 0.05 to 0.5 times the thickness,
  at least one of the inlet-side container element and the outlet-side container element is provided with a rib on an inner surface, the rib being pressed against the filtering surface of the filter element, and
  a coefficient of variation value of the thickness of the filter element is 6% or less.

10. The blood processing filter according to claim 1, wherein at least one of the inlet-side container element and the outlet-side container element is provided with a plurality of ribs including the rib, and
  the ribs are configured to extend linearly and be arranged parallel to each other.

11. The method of manufacturing the blood processing filter according to claim 9, wherein at least one of the inlet-side container element and the outlet-side container element is provided with a plurality of ribs including the rib, and
  the ribs are configured to extend linearly and be arranged parallel to each other.

* * * * *